United States Patent [19]

Lindstrom et al.

[11] Patent Number: 4,593,691
[45] Date of Patent: Jun. 10, 1986

[54] ELECTROSURGERY ELECTRODE

[75] Inventors: Judy Lindstrom, Largo; W. Lane Ector, Jr., Clearwater; Arthur F. Trott, Largo, all of Fla.

[73] Assignee: Concept, Inc., Clearwater, Fla.

[21] Appl. No.: 513,440

[22] Filed: Jul. 13, 1983

[51] Int. Cl.⁴ .............................................. A61B 17/39
[52] U.S. Cl. ........................ 128/303.14; 128/303.15; 128/303.17; 219/234
[58] Field of Search ....................... 128/303.13–303.19, 128/800, 801, 741; 219/229, 230, 233–235, 238, 239; 433/32

[56] References Cited

U.S. PATENT DOCUMENTS

| | | | |
|---|---|---|---|
| 1,841,968 | 1/1932 | Lowry | 128/303.14 |
| 2,828,747 | 4/1958 | August | 128/303.14 |
| 2,888,928 | 6/1959 | Seiger | 128/303.17 |
| 3,807,404 | 4/1974 | Weissman et al. | 128/303.14 |
| 3,974,833 | 8/1976 | Durden, III | 128/303.17 |
| 4,014,343 | 3/1977 | Esty | 128/303.14 |
| 4,034,762 | 7/1977 | Cosens et al. | 128/303.17 |
| 4,103,688 | 8/1978 | Edwards | 128/303.17 |

FOREIGN PATENT DOCUMENTS

| | | | |
|---|---|---|---|
| 651428 | 12/1935 | Fed. Rep. of Germany | 128/303.17 |
| 2460481 | 6/1976 | Fed. Rep. of Germany | 128/303.13 |
| 896711 | 3/1945 | France | 128/303.18 |

OTHER PUBLICATIONS

Pao, "Coaxial Bipolar Probe" Arch. Ophthol. vol. 97, Jul. 1979, pp. 1351-1352.

Primary Examiner—Lee S. Cohen
Attorney, Agent, or Firm—Frijouf, Rust & Pyle

[57] ABSTRACT

An improved electrosurgery electrode is disclosed for cooperation with an electrode holder connected to a source of electrical power. The improved electrode comprises a solid electrode shaft having a first and a second end with a shaft connector electrically connecting the first end of the electrode shaft to the electrode holder. An electrode tip is disposed on the second end of the shaft with the electrode tip having a hook terminating in a distal end extending generally perpendicular to an axis extending through the electrode shaft. A shaft insulator provides a waterproof electrical insulation between an exposed portion of the electrode tip and the shaft connector. The shaft connector may optionally enable removal or interchange of the electrodes in the electrode holder to accommodate for various types of electrosurgery techniques such as a subcutaneous lateral release or a meniscectomy procedure through an arthroscopic system.

14 Claims, 18 Drawing Figures

ELECTROSURGERY ELECTRODE

BACKGROUND OF THE INVENTION

1. Field of the Invention

This invention relates to medical appliances and more specifically to electrosurgery suitable for use with an arthroscopic system.

2. Information Disclosure Statement

The field of electrosurgery has undergone major and rapid advances since the early 1900's. In general, electrosurgery techniques have been utilized primarily in neurological and urological operations. The use of electrosurgical techniques in neurological and urological operations has produced improvements in both the configuration of the electrosurgical electrode as well as improvements in the electrical power generators powering the electrosurgical electrode. Electrosurgical power generators are now able to produce a wide range of power levels and frequencies which are now suitable for other types of electrosurgical techniques requiring higher power and/or control of current and voltage to the electrosurgical electrode.

With the advancements in the electrosurgical power generators, emphasis has been placed on the specialization of electrodes for specific electrosurgical techniques to enable more accurate electrosurgical operations. The widespread application of arthroscopic devices has also revolutionized the use of electrosurgery enabling many operations to now be accomplished with minimal external incisions and with superior control of coagulation and cutting through precisely controlled electrosurgical generators and specifically designed electrosurgical electrodes.

Many in the prior art have designed specific electrosurgical electrode configurations for specific electrosurgical techniques. U.S. Pat. No. 2,090,923 to Wappler discloses an electrodic endoscopic instrument in which a fenestrated endoscopic sheath is provided with means for longitudinally advancing and retracting an electrode rod with the rod having an operative electrode at the forward end protruding from the fenestra.

U.S. Pat. No. 4,149,538 to Mrava et al teaches the use a resectoscope electrode assembly with a non-conductive bearing tube and method of making the same wherein one section of the electrode takes the form of a pair of spaced parallel arms terminating in an arcuate cutting loop with the arms being encased in insulated sleeving to prevent arcing between the electrode arms.

U.S. Pat. No. 4,181,131 to Ogiu discloses a high frequency electrosurgical instrument for cutting human body cavity structures wherein an electrode is reciprocally mounted through a sheath enabling the electrode to be inserted through a channel in an endoscope and thereafter extended to provide a suitable cutting electrode.

U.S. Pat. No. 4,311,144 to Harada discloses an electrosurgical knife which may be inserted into a body cavity of a patient through an endoscope wherein the electrode is disposed within a flexible insulation tube with a metal sheath encasing the electrode with the metal sheath being in electrical contact with the skin of the patient.

Although the aforementioned prior art references have aided in the development of electrosurgery, none of the aforementioned advances has satisfied the needs in the treatment and management of joint disorders in orthopedic practice. The use of arthroscopy in orthopedic practice has enabled orthopedic surgeons to directly visualize injury and disease sites and correct conditions with a minimal incision which only a few years ago would require an extensive open incision. However, the advent of arthroscopic surgery in orthopedic practice has posed new problems to the manufacturers of electrosurgical equipment, namely the control of bleeding and the difficulty of dividing the tough avascular tissues encountered in the joints.

G. Klaud Miller, M.D. et al has disclosed the advantages of electrosurgery in orthopedic practice in a paper entitled "The Use of Electrosurgery for Arthroscopic Subcutaneous Lateral Release" published by Charles B. Slack, Inc., Medical Publisher, (1982).

It is a primary objective of this invention to provide an apparatus which overcomes the aforementioned difficulties of the prior art devices and provides an improvement which is a substantial contribution to the advancement of electrosurgical electrode art.

Another object of this invention is to provide an improved electrosurgical electrode which is applicable to many types of surgical operations but is specifically designed for a subcutaneous lateral release as well as meniscectomy operations.

Another object of this invention is to provide an improved electrosurgical electrode wherein the electrode is interchangeable with an electrode holder and wherein the electrode and the electrode holder may be manufactured as a disposable medical appliance.

Another object of this invention is to provide an improved electrosurgical electrode comprising a solid electrode shaft having an electrode tip at the terminal end thereof with the distal end of the electrode tip comprising a hook extending generally perpendicular to an axis extending through the electrode shaft.

Another object of this invention is to provide an improved electrosurgical electrode wherein the electrode shaft is insulated between the active electrode tip and the electrode holder.

Another object of this invention is to provide an improved electrosurgical electrode wherein the electrode shaft and electrode tip having a hook configuration may be inserted into the patient through a conventional introducer for an arthroscopic operation.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention within the scope of the invention. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention may be incorporated into an apparatus comprising an electrosurgical electrode having a first and a second end for cooperation with an electrode holder connected to an electrical power source. A shaft connecting means is provided for electrically connecting the first end of the shaft to the electrode holder. An electrode tip having a proximal end and a distal end. The distal end of the electrode tip comprising a hook which extends generally perpendicular to an axis which extends through the electrode shaft. Insulating means provides electrical insulation between the exposed portion of the electrode tip and the shaft connecting means.

In a more specific embodiment of the invention, the shaft connecting means includes means for removably connecting the shaft to the electrode holder. An insulating hub is disposed proximate the first end of the shaft for insulating the shaft connecting means. The hub includes a through aperture for receiving the first end of the electrode shaft and incorporates an internal taper for cooperating with an external taper on the electrode holder to provide an electrically insulated seal between the shaft and the electrode holder. The second end of the electrode shaft includes a bore axially extending into the shaft for receiving a base (proximal end) of the electrode tip. The electrode tip is preferably secured in the bore by radially inwardly crimping the second end of the electrode shaft into engagement with the electrode tip. The electrode tip may be tapered toward the distal end and covered by a tip insulating means to expose only the distal end of the electrode tip. The electrode tip may alternately comprise a hooked blade.

In another embodiment of the invention, the insulating hub includes an undercut portion on the outer periphery thereof with a shaft tubing means extending from the electrode tip to overlay the undercut portion. The shaft tubing means may include a unitary shaft tubing or, in the alternative, a first shaft tubing engaging the shaft with a second shaft tubing overlaying the first shaft tubing.

The invention may also be incorporated into the method of forming an electrode blade including the steps of providing a conically shaped electrode, bending the electrode to form a hook, and deforming the bent electrode to form a hooked blade.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts through the several views of the drawings.

DETAILED DESCRIPTION

Figure 1:
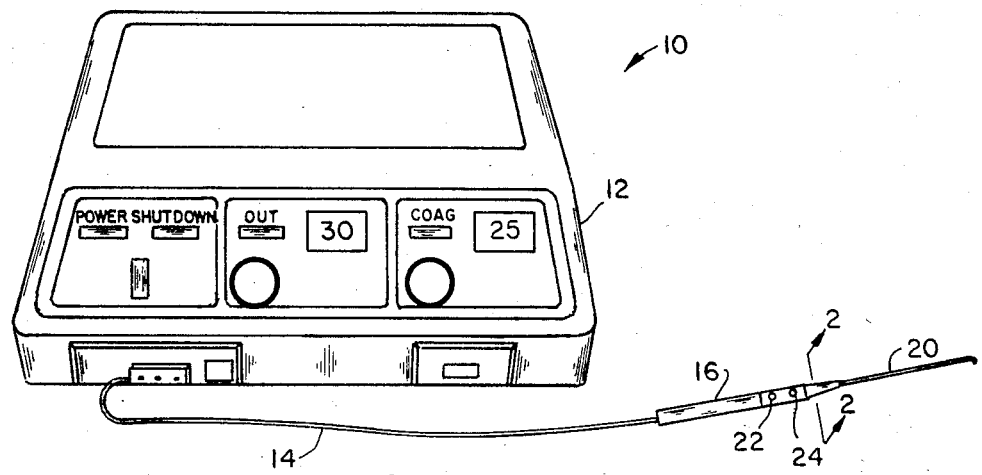
FIG. 1 is a perspective view of an electrical surgical apparatus incorporating the present invention.

FIG. 1 is an elevational view of an electrosurgical apparatus 10 comprising an electronic control power source typically a radio frequency generator 12 connected by an electrical connector 14 to an electrode holder 16. In this embodiment, the electronic control power source 12 is a monopolar device with one polarity of electrical voltage being furnished through electrical connector 14 and with a second electrical connector (not shown) normally connected through a dispersive electrode to the patient. Although a specific example has been shown for the electronic control power source, the power source, per se, does not form a part of the invention as will be apparent hereinafter.

The electrode holder 16 is electrically connected to an electrode 20 through activating switches shown as push button switches 22 and 24. First switch 24 provides sufficient power to electrode 20 for cutting tissue whereas second switch 22 provides limited power to electrode 20 for coagulation. Multiple switches 22 and 24 on the electrode holder 16 enable cutting or coagulating by the surgeon with the electrosurgical electrode 20.

Figure 2:
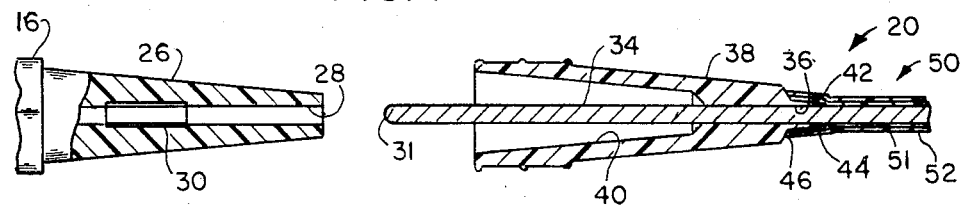
FIG. 2 is an enlarged partial sectional view along line 2—2 of FIG. 1.

FIG. 2 is an enlarged exploded sectional view generally along the line 2—2 of FIG. 1 illustrating the electrode holder 16 having an external taper 26 and an axial aperture 28. The electrode holder 16 is preferably made of an insulating plastic material with a resilient metallic electrical connector 30 connected to switches 22 and 24 (not shown) and disposed within the electrode holder 16. Shaft connecting means comprising a rounded first end 31 of a solid electrode shaft 34 is received within an aperture 36 of an insulating hub 38 preferably made of an insulating plastic material. The insulating hub 38 includes an internal taper 40 which cooperates in a sealing relationship with the external taper 26 of the electrode holder 16 when the first end 31 of solid electrode shaft 34 is inserted within axial aperture 28 of the electrode holder 16 to electrically contact electrical connector 30. A substantially waterproof seal is established between the internal taper 40 and external taper 26.

The insulating hub 38 includes an undercut portion 42 comprising a surface 44 extending generally axially along solid shaft 34 and defined by a shoulder 46. The undercut portion 42 is established to receive shaft insulation means 50 shown as a first shaft tubing 51 in direct engagement with the solid electrode shaft 34 and a second shaft tubing 52 which overlays the first shaft tubing 51. The shaft insulation means 50 extends upon surface 44 and engages shoulder 46 to provide a watertight seal between the shaft tubing insulation means 50 and insulating hub 38. Preferably, the shaft tubing insulation is a heat shrinkable tubing as will be described in greater detail hereinafter. Furthermore, although the shaft tubing insulation has been disclosed as a first and second shaft tubing insulation, it should be appreciated that a single tubing insulation may be incorporated within the present invention. Irrespective of whether a single or multiple shaft tubing insulation is utilized, it is important that the outer surface of the shaft tubing insulation be resistant to abrasion normally encountered in the surgical procedure. This abrasion resistance will maintain the electrical insulation characteristic of the shaft tubing insulation and reduce the possibility of undesired electrical leakage through the insulation due to abrasion occuring during the operating procedure.

Figure 3:
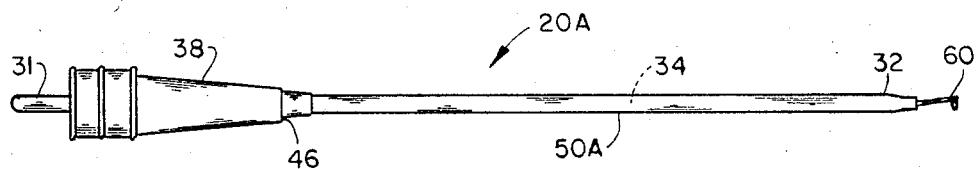
FIG. 3 is an enlarged side view of a first embodiment of an improved electrode suitable for use with the apparatus shown in FIG. 1.

FIG. 3 is an enlarged elevational view of a first embodiment of an improved electrosurgical electrode 20A. The insulating hub portion 38 is identical to the embodiment shown in FIG. 2. The solid electrode shaft 34 within the shaft tubing insulation means 50 includes a second end 32 receiving an electrode tip 60 which will be described in greater detail in reference to FIGS. 4-6.

Figure 4:
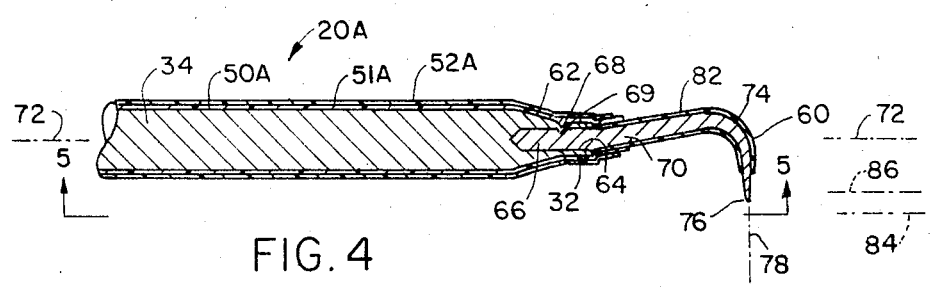
FIG. 4 is an enlarged sectional view of a portion of the electrode shown in FIG. 3.
Figure 5:
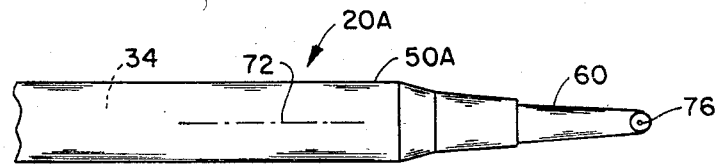
FIG. 5 is an elevational view along line 5—5 in FIG. 4.

FIG. 4 is an enlarged sectional view of a portion of the electrode shown in FIG. 3 with FIG. 5 being an elevational view along line 5—5 in FIG. 4. The solid electrode shaft 34 is tapered by a taper 62 at the second end 32. The second end 32 includes an axial bore 64 for receiving an electrode tip base (proximal end) 66. The electrode tip base (proximal end) 66 is secured from axial movement from the axial bore 64 by a deformation 68 in the outer surface of the second end 32. The deformation 68 may be obtained by a swaging operation, the use of a center punch or the like. The electrode tip base (proximal end) 66 may be optionally deformed or crimped at 69 to receive the deformation 68.

The electrode tip 60 is tapered along the length thereof as shown in FIGS. 4–5 and includes a bend at 70 forming and angle of approximately 10° from an axis 72 extending through the solid electrode shaft 34. The electrode tip 60 also includes a bend at 74 of approximately 100° establishing the distal end 76 of the electrode tip 60 to have an axis thereof 78 established approximately 90° relative to the axis 72 extending through the solid electrode shaft 34.

A tip insulator 82 insulates the tapered electrode tip 60 from an area approximate the base 66 to expose only a portion of electrode tip 60 adjacent the distal end 76 as shown in FIG. 4. The tip insulator 82 is overlayed by the shaft insulation means 50A and specifically first shaft tubing 51A and second shaft tubing 52A to provide a watertight electrical seal of the electrode tip 60 and electrode shaft 34 with only the distal end 76 of the electrode tip 60 being exposed.

In a specific example of the electrode 20 shown in FIGS. 3–5, the solid shaft 34 is preferably made of Type 300 series stainless steel with the electrode tip 60 fashioned from a conical blank of a cobalt chromium alloy material. The distal end 76 preferably has a spherical radius of 0.007 inches with a Teflon tip insulator 82 exposing from approximately 0.040 inches to 0.050 inches. This exposure has been found to be optimal since a much greater exposure will cause the electrical energy to dissipate whereas a much lesser exposure will concentrate the electrical energy in a confined area.

The embodiment shown in FIG. 4 utilizes a soft polyolefin shrink tubing for the first shaft tubing 51A and a polyvinylidene fluoride sold under the trademark KYNAR by Raychem Corporation for the second shaft tubing 52A. The first shaft tubing prevents leakage of electrical energy especially radio frequency power along the solid shaft 34. Additionally, the first shaft tubing seals the first and second ends 31 and 32 of solid shaft 34 to provide a water tight seal. The second shaft tubing 52A overlays the first shaft tubing 51A to provide additional resistance to abrasion.

Figure 6:
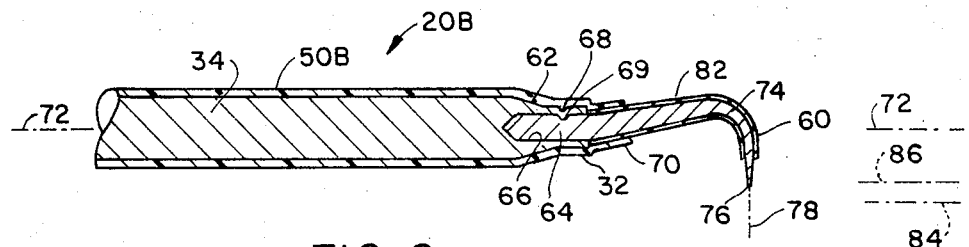
FIG. 6 is a sectional view similar to FIG. 4 showing a modification of the first embodiment of the electrode.

FIG. 6 is an enlarged sectional view similar to FIG. 4 illustrating a variation of the electrode of FIG. 3. In this embodiment, a single shaft tubing 50B is utilized for effecting the insulation of solid shaft 34. The single shaft tubing 50B may be a semi-rigid polyolefin tubing as described in Raychem specification RT-1190/3. The thickness of the shaft tubing 50 should be sufficient to prevent electrical leakage of the radio frequency signal generated by the power source 12. Preferably this thickness may be in the range of 0.013 inch to 0.017 inch.

The distal end 76 as illustrated by phantom line 84 extends beyond the surface of the electrode 20 as illustrated by the phantom line 86 a distance less than the radius of the electrode 20 as represented by the distance between axis 72 and phantom line 86. This diameter of the configuration enables the electrode tip 60 to have a low axial profile to provide strength and rigidity while permitting passage through an introducer cannula.

Figure 7:
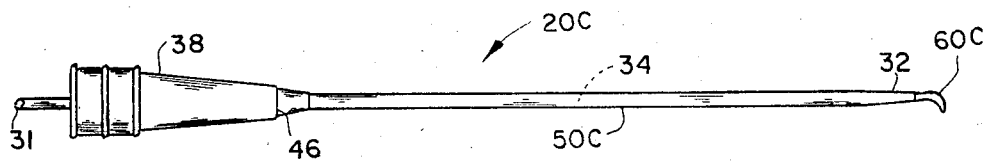
FIG. 7 is an enlarged side view of a second embodiment of an improved electrode suitable for use with the apparatus shown in FIG. 1.

FIG. 7 is an enlarged elevational view of a second embodiment of an improved electrosurgical electrode 20C. The insulating hub portion 38 is identical to the embodiment shown in FIG. 2. The solid electrode shaft 34 within the shaft tubing insulation means 50C includes a second end 32 receiving an electrode tip 60C which will be described in greater detail in reference to FIGS. 8-14.

Figure 8:
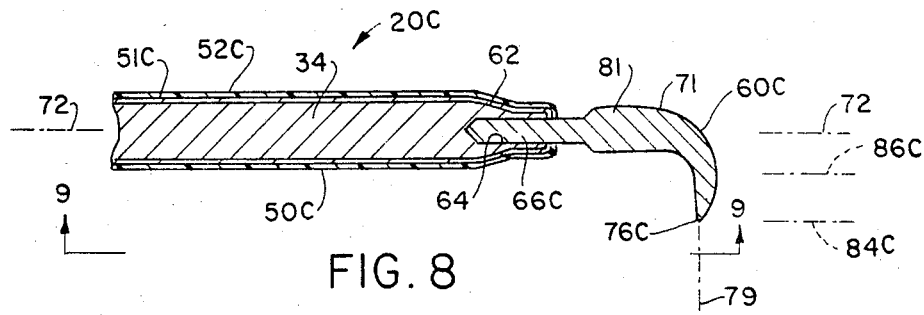
FIG. 8 is an enlarged sectional view of a portion of the electrode shown in FIG. 7.
Figure 9:
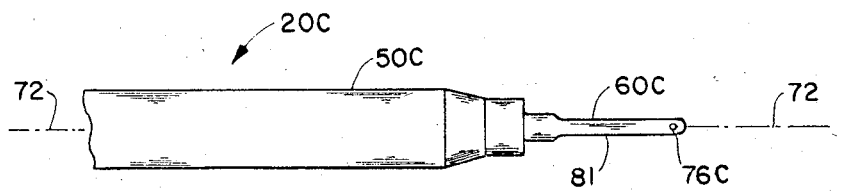
FIG. 9 is an elevational view along line 9—9 of FIG. 8.

FIG. 8 is an enlarged sectional view of a portion of the electrode shown in FIG. 7 with FIG. 9 being an elevational view along the line 9—9 in FIG. 8. The solid electrode shaft 34 is tapered by a taper 62 at the second end 32. The second end 32 includes an axial bore 64 for receiving an electrode tip base (proximal end) 66C. The electrode tip base (proximal end) 66C is secured in the axial bore 64 by suitable means as set forth in reference to FIG. 4.

The electrode tip 60C is tapered along the length thereof as shown in FIG. 8 and includes a bend at 71 of approximately 90° establishing the distal end 76C of the electrode tip 60C to have an axis thereof 79 established approximately 90° relative to the axis 72 extending through the electrode shaft 34. The electrode tip 60C is formed in a hooked configuration having a blade 81.

In a specific embodiment of the electrode 20C shown in FIGS. 7-9, the solid shaft 34 and conical shaped blade blank are made of Series 300 stainless steel. The distal end 76C has a spherical radius approximately of 0.007 inches.

The embodiment of FIGS. 7-9 utilizes a soft polyolefin shrink tubing for the first shaft tubing 51C and a polyvinylidene fluoride tubing for the second shaft tubing 52C in a manner similar to FIG. 4.

Figure 10:
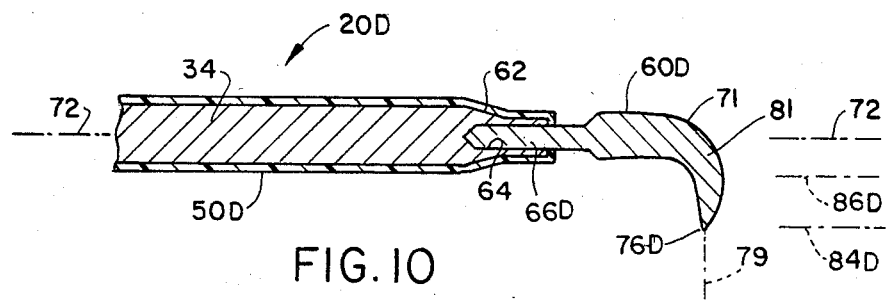
FIG. 10 is a sectional view similar to FIG. 8 showing a modification of the second embodiment of the electrode.

FIG. 10 is essentially identical to FIG. 8 but utilizes a single shaft tubing of semi-rigid polyolefin tubing in a manner similar to FIG. 6.

The distal end 76C as illustrated by the phantom line 84C extends beyond the surface of electrode 20C as illustrated by the phantom line 86C a distance generally equal to the radius of the electrode 20C as represented by the distance between axis 72 and phanton line 86. This diameter of the configuration enables the electrode tip 60C to be passed through an introducer catheter.

FIGS. 11-14 illustrate the steps of making the electrode tip 60C shown in FIGS. 7-10. Although the process is shown with the electrode tip 60C attached to the electrode shaft 34, it should be understood that the process may be performed prior to securing the electrode tip 60C to the solid shaft 34.

Figure 11:
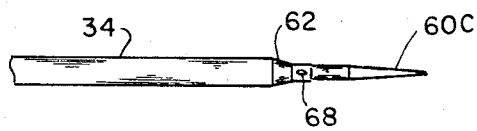
FIG. 11 illustrates a first step in the method of making the electrode shown in FIGS. 7-10.

FIG. 11 illustrates the conical blank electrode before the processing.

Figure 12:
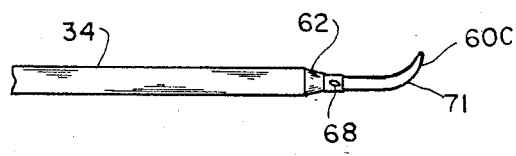
FIG. 12 is a second step in the method of making the electrode of FIGS. 7-10.

FIG. 12 shows the bending of the conical blank electrode 60C at 71 to provide a substantially 90° bend with the axis 79 of the distal end 76 being perpendicular to the axis 72 of solid shaft 34 as shown in FIG. 8.

Figure 13:
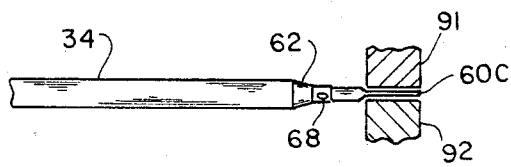
FIG. 13 is the third step in the process of making the electrode shown in FIGS. 7-10.

FIG. 13 illustrates dies 91 and 92 comprising the bent conical blank to provide the blade 81 having a substantially uniform thickness as shown in FIG. 13.

Figure 14:
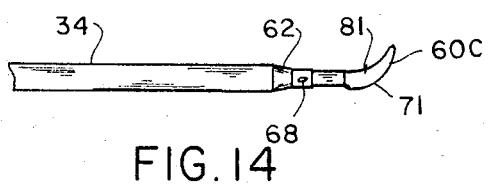
FIG. 14 illustrates the completed electrode as shown in FIGS. 7-10.

FIG. 14 shows the complete electrode tip 60C awaiting the application of the shaft tubing 50C or 50D.

Although the two embodiments of the improved electrodes shown in FIGS. 3-6 and FIGS. 7-10 may find a wide variety of applications, the electrode shown in FIGS. 3-6 finds particular value in meniscectomy procedures whereas the electrode shown in FIGS. 7-10 finds particular value in a subcutaneous lateral release.

Figure 15:
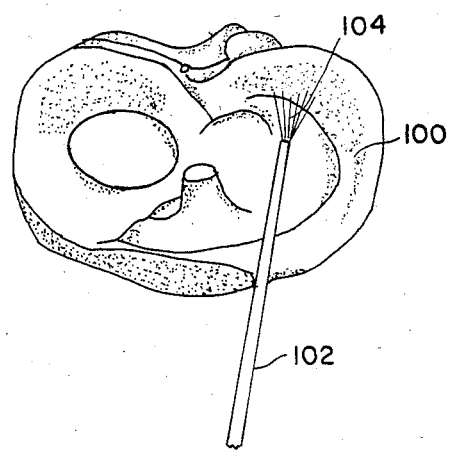
FIG. 15 illustrates an internal view of a knee joint of a patient under arthroscopic examination.

FIG. 15 illustrates the interior knee joint 100 of a patient undergoing examination by an arthroscope 102 revealing a meniscal defect 104.

Figure 16:
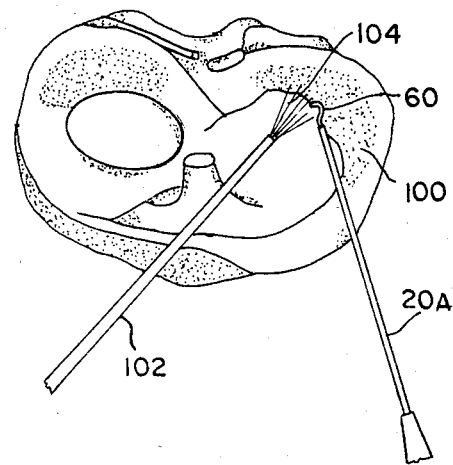
FIG. 16 is a view similar to FIG. 15 showing the use of the electrodes shown in FIGS. 3-6 in a meniscectomy procedure.

FIG. 16 shows the entry of the electrode 20A of FIGS. 3-6 with the electrode tip 60 excising the defect through electrosurgery to enable the subsequent removal of excised tissue from the joint. The specific configuration of the electrode tip 60 facilitates an easy excision of the tough cartilaginous tissue.

Figure 17:
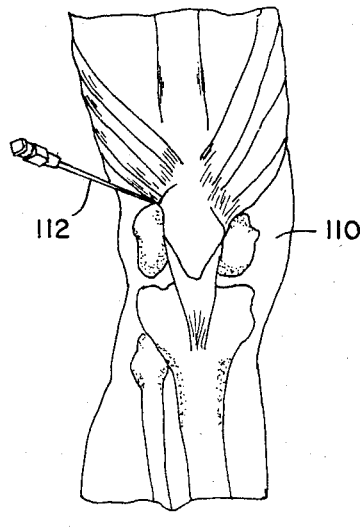
FIG. 17 illustrates an internal view of a knee joint.

FIG. 17 illustrates the interior knee joint and muscle tissue 110 with a landmark needle 112 marking the proximal limit of lateral release at the margin of the vastus lateralis.

Figure 18:
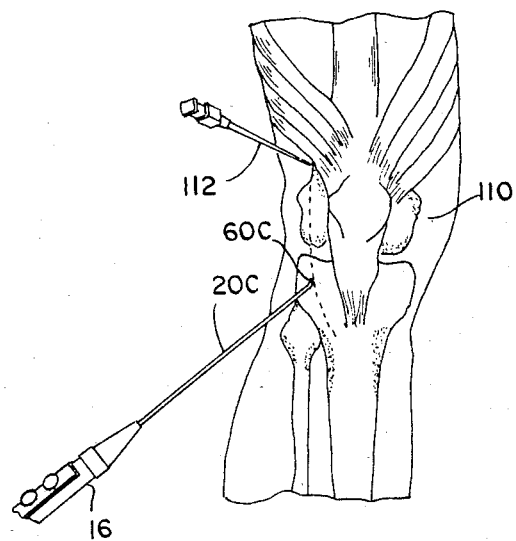
FIG. 18 is a view similar to FIG. 17 showing the use of the electrode in FIGS. 7-10 in a subcutaneous lateral release.

FIG. 18 shows the electrode shown in FIGS. 7-10 effecting release distally to the level of the tibial tubercle with the line of incision disposed approximately one centimeter to the border of the patella. The improved hemostasis as a result of the electrode accelerates rapid recovery of the patient and lowers patient morbidity.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An improved electrosurgery electrode for cooperation with an electrode holder connected to a source of electrical power and with an introducer catheter, comprising in combination:
   a solid electrode shaft having a first and a second end;
   a shaft connecting means for electrically connecting said first end of said electrode shaft to the electrode holder;
   an electrode tip having a proximal and distal end;
   said distal end of said electrode tip comprising a hook extending generally perpendicular from an axis extending through said electrode shaft;
   a tip connecting means for electrically connecting said proximal end of said electrode tip to said second end of said electrode shaft thereby electrically connecting said distal end of said electrode tip;
   said distal end of said electrode tip extending beyond the surface of said electrode shaft a distance generally equal to or less than the radius of said electrode shaft thereby enabling said electrode tip to pass through the introducer catheter; and
   insulating means for providing electrical insulation and abrasion resistance between an exposed portion of said electrode tip and said shaft connecting means and for forming a substantially waterproof seal when said first end of said electrode shaft is connected to the electrode holder.

2. An improved electrosurgery electrode as set forth in claim 20 wherein said shaft connecting means includes means for removably connecting said electrode shaft to the electrode holder.

3. An improved electrosurgery electrode as set forth in claim 20 wherein said insulating means includes an insulating hub disposed proximate said first end of said electrode shaft for insulating said shaft connecting means.

4. An improved electrosurgery electrode as set forth in claim 3 wherein said insulating hub includes an internal taper for cooperating with an external taper on the electrode holder to provide said electrical insulation between said shaft and the electrode holder.

5. An improved electrosurgery electrode as set forth in claim 3 wherein said insulating hub includes an aperture defined in said insulating hub;
   said aperture receiving said first end of said electrode shaft therein.

6. An improved electrosurgery electrode as set forth in claim 5 wherein;
   said insulating means includes shaft tubing means extending between said distal end of said electrode tip and said insulating hub;
   said shaft tubing means includes a first shaft tubing engaging said shaft;
   a second shaft tubing overlaying said first shaft tubing to provide additional abrasion resistance and;
   said insulating hub having an undercut portion on the outer periphery thereof with said shaft tubing means overlaying said undercut portion of said insulating hub.

7. An improved electrosurgery electrode as set forth in claim 1 wherein said tip connecting means includes said second end of said electrode shaft having a bore axially extending into said shaft;

said electrode tip extending into said bore; and means for securing said electrode tip in said bore.

8. An improved electrosurgery electrode as set forth in claim 7 wherein said means for securing said electrode tip in said bore includes radially inwardly crimping said second end of said electrode shaft into engagement with said electrode tip.

9. An improved electrosurgery electrode as set forth in claim 1 wherein the cross-sectional area of said electrode tip is tapered toward said distal end of said electrode tip.

10. An improved electrosurgery electrode for as set forth in claim 1 including tip insulating means for insulating said electrode tip to expose only the distal end of said electrode tip from approximately 0.04 inches to 0.05 inches.

11. An improved electrosurgery electrode as set forth in claim 1 wherein said electrode tip comprises a hooked blade.

12. An improved electrosurgery electrode for cooperation with an electrode holder connected to a source of electrical power and with an introducer catheter, comprising in combination:

a solid electrode shaft having a first and a second end;

a shaft connecting means for electrically connecting said first end of said electrode shaft to the electrode holder;

an insulating hub disposed proximate said first end of said electrode shaft for insulating said shaft connecting means and for forming a substantially waterproof seal when said first end of said electrode shaft is connected to the electrode holder;

said insulating hub including an aperture defined in said insulating hub with said aperture receiving said first end of said electrode shaft therein;

an electrode tip having a proximal and distal end;

said distal end of said electrode tip comprising a hook extending generally perpendicular from an axis extending through said electrode shaft;

said second end of said electrode shaft including a bore axially extending into said shaft with said proximal end of said electrode tip extending from said bore, electrically connecting said distal end of said electrode tip to said second end of said electrode shaft;

said distal end of said electrode tip extending beyond the surface of said electrode shaft a distance generally equal to or less than the radius of said electrode shaft thereby enabling said electrode tip to pass through the introducer catheter; and an insulating shaft tubing means for providing an electrical insulation between an exposed portion of said electrode tip and said insulating hub.

13. An improved electrosurgery electrode as set forth in claim 12 including tip insulating means for insulating said electrode tip to expose only the distal end of said electrode tip from approximately 0.04 inches to 0.05 inches.

14. An improved electrosurgery electrode as set forth in claim 1 wherein said electrode tip comprises a hooked blade wherein said distal end has a spherical radius of approximately 0.007 inches.

* * * * *